US010402417B2

(12) United States Patent
Kulshreshtha et al.

(10) Patent No.: US 10,402,417 B2
(45) Date of Patent: Sep. 3, 2019

(54) SYNTHESIZING DATA SOURCES (71) Applicant: Microsoft Technology Licensing, LLC, Redmond, WA (US)

(72) Inventors: Jitendra Kulshreshtha, Redmond, WA (US); Avon Fernandes, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 177 days.

(21) Appl. No.: 15/478,972

(22) Filed: Apr. 4, 2017

(65) Prior Publication Data

US 2018/0225342 A1     Aug. 9, 2018

Related U.S. Application Data (60) Provisional application No. 62/456,861, filed on Feb. 9, 2017.

(51) Int. Cl.

| | | |
|---|---|---|
| *G06F 16/00* | (2019.01) | |
| *G06F 16/248* | (2019.01) | |
| *A61B 5/01* | (2006.01) | |
| *A61B 5/11* | (2006.01) | |
| *A63B 24/00* | (2006.01) | |
| *G06F 16/22* | (2019.01) | |
| *G06F 16/2455* | (2019.01) | |
| *A61B 5/00* | (2006.01) | |
| *G16H 50/00* | (2018.01) | |

(Continued)

(52) U.S. Cl.
CPC .......... *G06F 16/248* (2019.01); *A61B 5/0022* (2013.01); *A61B 5/01* (2013.01); *A61B 5/1118* (2013.01); *A63B 24/0062* (2013.01); *G06F 16/22* (2019.01); *G06F 16/2455* (2019.01); *G06F 16/25* (2019.01); *G16H 50/00* (2018.01); *A61B 5/02438* (2013.01); *A61B 5/4809* (2013.01); *A61B 2560/0242* (2013.01); *A63B 2220/17* (2013.01); *A63B 2220/20* (2013.01); *A63B 2220/30* (2013.01); *A63B 2225/20* (2013.01); *A63B 2225/50* (2013.01); *A63B 2230/06* (2013.01); *A63B 2230/50* (2013.01); *A63B 2230/75* (2013.01)

(58) Field of Classification Search
None
See application file for complete search history.

(56) References Cited

U.S. PATENT DOCUMENTS

| | | |
|---|---|---|
| 8,849,610 B2 | 9/2014 | Molettiere et al. |
| 9,224,311 B2 | 12/2015 | Yeh et al. |

(Continued)

OTHER PUBLICATIONS

"Environmental Factors Influencing Human Performance", https://www.google.co.in/url?sa=t&rct=j&q=&esrc=s&source=web&cd=&cad=rja&uact=8&ved=0ahUKEwjywvbQuNzRAhUGvl8KHbqCBZUQFggkMAe&url=https%3A%2F%2Fwww.iaaf.org%2Fdownload%2Fdownload%3Ffilename%3Da5e2cf82-73d7-477b-bba5-280669f8ae0f.pdf%26urlslug%3DChapter%252011%25253A%2520Environmental%2520factors%2520influencing%2520human%.

(Continued)

*Primary Examiner* — Son T Hoang
(74) *Attorney, Agent, or Firm* — Shwegman Lundberg & Woessner, P.A.

(57) ABSTRACT

In example embodiments, a machine accesses metadata items from multiple different sources associated with a user. The machine determines that metadata items from two or more sources are related to an event of the user, the two or more sources being from among the multiple different sources. The machine stores the metadata items from the two or more of the sources in conjunction with the event.

16 Claims, 6 Drawing Sheets

(51) Int. Cl.
*G06F 16/25* (2019.01)
*A61B 5/024* (2006.01)

(56) References Cited

U.S. PATENT DOCUMENTS

| | | |
|---|---|---|
| 2012/0172677 A1 | 7/2012 | Logan et al. |
| 2012/0282995 A1* | 11/2012 | Allen ................ G06Q 30/0214 |
| | | 463/22 |
| 2015/0314166 A1 | 11/2015 | Hong et al. |
| 2016/0151603 A1 | 6/2016 | Shouldice et al. |
| 2016/0151668 A1* | 6/2016 | Barnes .................... G09B 7/02 |
| | | 706/46 |
| 2016/0196758 A1 | 7/2016 | Causevic et al. |
| 2016/0270718 A1 | 9/2016 | Heneghan et al. |
| 2016/0353235 A1* | 12/2016 | Williams ................ H04W 4/02 |
| 2016/0367187 A1 | 12/2016 | William et al. |
| 2016/0374567 A1 | 12/2016 | Breslow et al. |

OTHER PUBLICATIONS

Guerrache, et al., "Multiple Sensor Fusion approach to Map Environmental Noise Impact on Health", In Proceedings of the ACM International Joint Conference on Pervasive and Ubiquitous Computing, Sep. 12, 2016, pp. 1074-1078.

* cited by examiner

SYNTHESIZING DATA SOURCES

PRIORITY CLAIM

This application claims priority to U.S. Provisional Patent Application No. 62/456,861, filed on Feb. 9, 2017, and titled "SYNTHESIZING DATA SOURCES," the entire disclosure of which is incorporated herein by reference.

BACKGROUND

People do not understand the impact of external factors (e.g., weather, travel, allergies, diet, daylight) on events (e.g., run, sleep, bike, workout). When people study their performance, relative to events, they are not aware of external factors, which may be impacting their performance. As the foregoing illustrates, techniques for obtaining and displaying data relating external factors to metadata about events may be desirable.

BRIEF DESCRIPTION OF THE DRAWINGS

Some embodiments of the technology are illustrated, by way of example and not limitation, in the figures of the accompanying drawings.

SUMMARY

The present disclosure generally relates to machines configured for subjective health data collection, including computerized variants of such special-purpose machines and improvements to such variants, and to the technologies by which such special-purpose machines become improved compared to other special-purpose machines that provide technology for synthesizing data sources. In particular, the present disclosure addresses systems and methods for subjective health data collection.

According to some aspects, a machine accesses a set of events and metadata related to the set of events, the set of events and the metadata being generated by a client device. The machine accesses, from one or more data repositories distinct from the client device, a set of external factors related to the set of events. The machine correlates, using the one or more processors, the metadata related to the set of events with one or more external factors to generate a correlation. The machine transmits an output representing the generated correlation for display.

According to some aspects, a machine receives, at one or more processors and from a client device of a specified user, metadata about an event of the specified user. The machine accesses, from one or more data repositories distinct from the client device, external factors related to the event of the specified user. The machine accesses metadata about other events and external factors related to the other events of the specified user or of one or more different users. The machine correlates event metadata with the external factors to generate a correlation. The machine determines, based on the generated correlation, how the external factors related to the event of the specified user impacted the metadata about the event of the specified user to generate a report. The machine provides an output of the generated report, the output being provided in real-time upon receiving the metadata about the event of the specified user.

According to some aspects, a machine receives, at one or more processors, an input representing goals of a user with respect to events. The machine accesses, at the one or more processors, a correlation of metadata of events to external factors for the user or other users. The machine accesses, at the one or more processors, predicted future external factors for the user. The machine computes, based on the correlation and the predicted future external factors, optimal future times for scheduling the events. The machine provides an output of the computed optimal future times.

DETAILED DESCRIPTION

Overview

The present disclosure describes, among other things, methods, systems, and computer program products that individually provide various functionality. In the following description, for purposes of explanation, numerous specific details are set forth in order to provide a thorough understanding of the various aspects of different embodiments of the present disclosure. It will be evident, however, to one skilled in the art, that the present disclosure may be practiced without all of the specific details.

As noted above, people do not understand the impact of external factors (e.g., weather, travel, allergies, diet, daylight) on events (e.g., run, sleep, bike, workout). When people study their performance, relative to events, they are not aware of external factors, which may be impacting their performance.

In some aspects of the subject technology, a machine (e.g., a fitness tracker with a input/output component, a mobile phone, a tablet computer, a laptop computer, a desktop computer, a server, and the like) takes as input a set of events (e.g., data events generated from run, sleep, bike, workout activities) and metadata about the events (e.g., metadata that indicates heart rate, distance run, time spent running, calories burned, and the like). The events and their metadata may be manually entered by the user or received from a fitness tracker. The machine receives information about external factors (e.g., weather, travel, allergies, diet, daylight) related to the events from multiple different sources (e.g., online data repositories, a calendar associated with the user, input provided by the user, etc.). The machine correlates the metadata about the events with the external factors and provides an output representing the relationship between the metadata about the events and the external factors to the user.

Some users may desire access to information about the impact of external factors on their events in real-time. In some implementations, after a user completes an event the user uploads metadata about the event to the machine (which may be a fitness tracker, a mobile phone, a laptop, a remote online server machine, and the like). The machine accesses information about external factors related to the event from multiple different sources. The machine also accesses information about other events/external factors of the user and of other similar users. The machine provides, in real-time, a report to the user of how external factors influenced the user's event. The report is based on the accessed information about other events/external factors of the user and of other similar users.

Some users may set goals for themselves regarding events (e.g., a user may want to run three times per week and workout two times per week). Selecting optimal times for these events may be desirable.

According to some implementations, a machine takes as input the user's goals and how the user's events relate to external factors. The machine computes optimal times for the events based on predicted external factors (e.g., predicted weather and the user's travel plans) and the user's schedule. The machine may determine an optimal event plan based on the predicted external factors (e.g., indoor workouts may be planned for days which are predicted to be rainy and outdoor runs may be planned for days which are predicted to be sunny).

Some aspects of the subject technology are focused on the engineering design of combining aggregating data from disparate data sources and synthesizing them into one event. As used herein, an event includes an action or occurrence recognized by a computing system that is handled by the computing system. Such events may be generated or triggered by the system, by the user, or in other ways. For example, in a form, an event may include a button being clicked, the mouse moving, text being entered into text fields, the programming closing, and the like. According to some examples, events are objects in the programming language Java or another programming language. They come from a series of classes stored in java.util.EventObject (or another series of classes or different programming language structure).

As used herein, an event (e.g., exercise performance or performance in a goal-related activity) may include an exercise performance or any other physiologically tracked event. An event may include any physiological activity of the specified user. For example, an event may include running, sleeping, biking, or working out. The event may be associated with metadata (e.g., heartrate during event, distance run, amount of time spent sleeping, measures of quality of sleep, and the like).

Example Implementations

Figure 1:
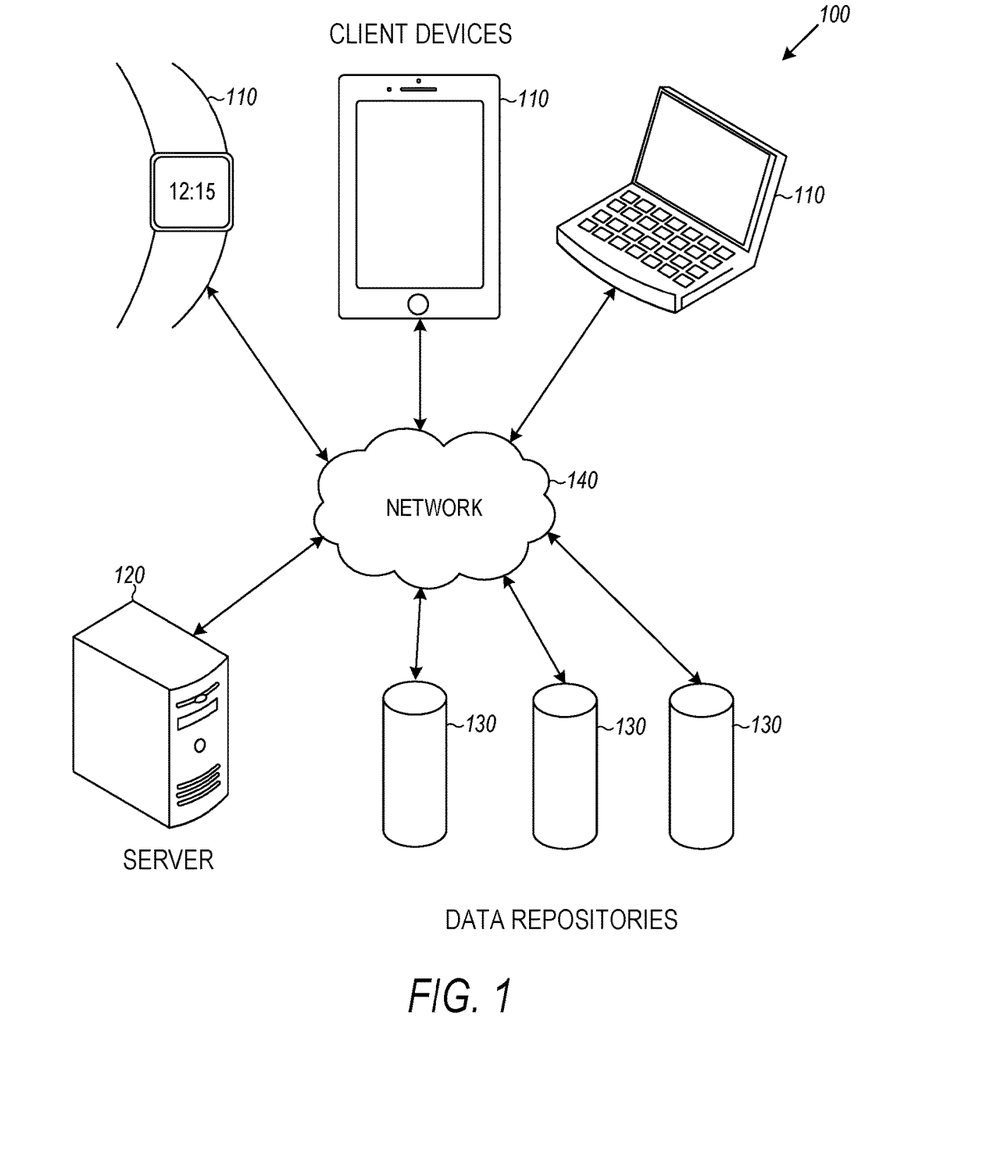
FIG. 1 illustrates an example system in which health data may be collected and stored, in accordance with some embodiments.

FIG. 1 illustrates an example system 100 in which health data may be collected and stored, in accordance with some embodiments. As shown, the system 100 includes client devices 110, a server 120, and data repositories 130 connected to one another via a network 140. The network 140 may include one or more of the Internet, an intranet, a local area network, a wide area network, a wired network, a wireless network, a virtual private network (VPN), a cellular network, a Wi-Fi network, and the like.

As shown in FIG. 1, the client devices 110 includes a fitness tracker, a mobile phone, and a desktop computer. The client devices 110 may include multiple such devices, as well as other devices that include a processor and a memory, such as a laptop computer, a tablet computer, a smart watch, and the like. A set of client devices 110 may be associated with a user, for example, when the user connects the client devices 110 to a user account. The fitness tracker may include software or hardware for measuring health or exercise metrics, such as a heart rate, a skin temperature, a sleep metric, a distance travelled, a speed, a number of calories burned, and the like. The fitness tracker includes a network interface for transmitting the measured metrics via the network 140. Some fitness trackers also include a user input/output device, such as a touchscreen.

The data repositories 130 may include any databases or data storage units. One or more of the data repositories 130 may store health or exercise metrics associated with users from the fitness tracker(s), calendars storing business or personal activities of users, weather data and weather forecasts, traffic data and traffic forecasts, and the like. The data repositories 130 may be distinct from the client devices 110.

The server 120 may include a single server machine or multiple machines in a server farm. The server 120 includes one or more processors and a memory. The one or more processors are configured (e.g., via software stored in the memory or via the hardware of the one or more processors) to implement all or a portion of the methods described in conjunction with FIGS. 2-5.

Figure 2:
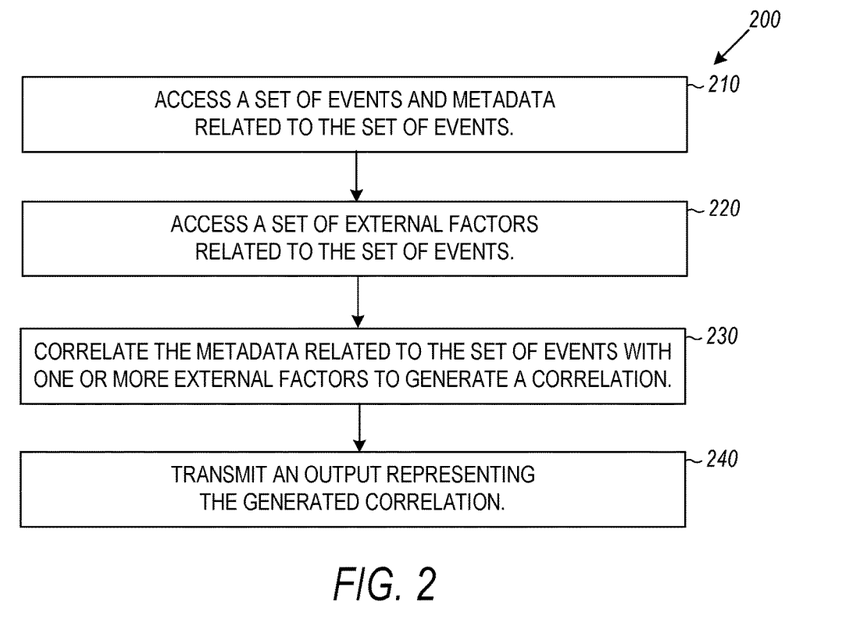
FIG. 2 is a flow chart illustrating an example method for relating events with external factors, in accordance with some embodiments.

FIG. 2 is a flow chart illustrating an example method 200 for relating events (e.g., exercise performance or performance in a goal-related activity) with external factors, in accordance with some embodiments. The method 200 may be implemented at a machine, such as the client device 110 or the server 120.

At operation 210, the machine accesses a set of events (e.g., physiological activity) and metadata related to the set of events. The set of events includes one or more of a run event, a sleep event, a bike event, a workout event, and the like. The set of events are generated by a client device 110, such as a fitness tracker or any other client device. The metadata related to the set of events may include data measured by a fitness tracker relating to the events, such as a heart rate, a skin temperature, a sleep metric, a distance travelled, a speed, a number of calories burned, and the like.

At operation 220, the machine accesses a set of external factors related to the set of events. The set of external factors includes one or more of weather, travel, allergies, diet, daylight, and the like. The set of external factors may be accessed from one or more of the data repositories 130. According to some examples, the set of external factors occurs contemporaneously with the set of events. As used herein, two moments occur contemporaneously if the time difference between the two moments is less than a predefined threshold time difference (e.g., one minute, one hour, one day, etc.). For example, if a man runs in Seattle at 7:45 AM on February 1, and the temperature in Seattle at 8:00 AM on February 1 is 2 C, then the man's running is contemporaneous with the temperature being 2 C. In some cases, the set of external factors are associated with a same geographic location (e.g., same city or same metropolitan area) as the set of events. For example, for a running event, the metadata may include heart rate, average and maximum speed, distance run, etc. The external factors may include the ambient temperature, the weather (e.g., sunny, cloudy, rainy, or snowy), the pollen count, and the like at the location where the running event took place.

At operation 230, the machine correlates the metadata related to the set of events with one or more external factors to generate a correlation. The correlation may be generated using any correlation technique, for example regression (e.g., linear regression, power regression, logarithmic regression, exponential regression, etc.) may be used.

At operation 240, the machine transmits an output representing the generated correlation for display at the client device 110 or a display unit. The output may be a graph illustrating the metadata of set of events and the external factor(s) correlated with the set of events. In one example implementation, the set of events includes a run event, the set of external factors includes an ambient temperature in a geographic region of the fitness tracker (or other client device), and the output includes a graph of the ambient temperature versus a distance run and a graph of the ambient temperature versus an average running speed. In another example implementation, the set of events includes a sleep event, the set of external factors includes a pollen count in a geographic region of the fitness tracker (or other client device), and the output includes a graph of the pollen count versus a number of hours of deep sleep.

Figure 3:
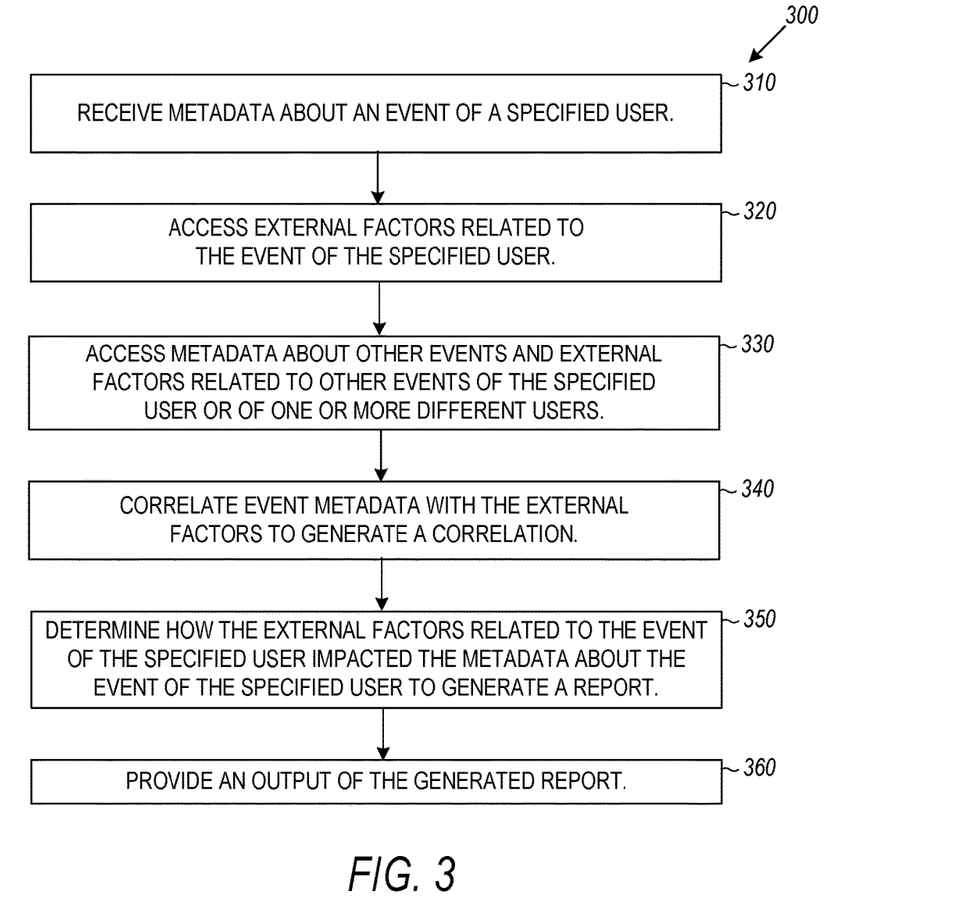
FIG. 3 is a flow chart illustrating an example method for demonstrating how external factors impact an event, in accordance with some embodiments.

FIG. 3 is a flow chart illustrating an example method 300 for demonstrating how external factors impact an event, in accordance with some embodiments. The method 300 may be implemented at a machine, such as the client device 110 or the server 120.

At operation 310, the machine receives metadata about an event of a specified user. The metadata may be received from a client device 110, such as a fitness tracker, of the specified user. The metadata may be measured (e.g., by the fitness tracker) or manually entered by the user (e.g., into an interface within a mobile application or browser application presented at the client device 110.

At operation 320, the machine accesses external factors related to the event of the specified user. The external factors may be accessed from one or more of the data repositories 130 external to the client device 110. The external factors may occur within a threshold time or within a threshold geographic distance of the event. The event may include a run event, a sleep event, a bike event, or a workout event. The external factors may include one or more of weather, travel, allergies, diet, and daylight.

At operation 330, the machine accesses metadata about other events and external factors related to the other events of the specified user or one or more different users. The one or more different users are identified based on the one or more different users having an age within a threshold number of years (e.g., five years) of the specified user, the one or more different users having a same gender as the specified user, or the one or more different users having a common geographic location (e.g., in the Seattle metro area or within a threshold distance, such as 10 km, 50 km or 100 km) with the specified user. In some cases, if little information about the user is available to the machine (e.g., if the user has been uploading his/her data to the machine or other machines accessible to the machine for less than one year), the data of the different users is accessed. Otherwise, only data about the user is accessed.

At operation 340, the machine correlates event metadata with the external factors to generate a correlation.

At operation 350, the machine determines, based on the generated correlation, how the external factors related to the event of the specified user impacted the metadata about the event of the specified user to generate a report.

At operation 360, the machine provides an output of the generated report. The output is provided in real-time upon receiving the metadata about the event of the specified user. The report may include a graph of one of the external factors versus the metadata about the event. The report may identify optimal conditions, relative to the external factors, for optimizing (e.g., minimizing, maximizing, or placing within an identified optimal range) the metadata of the event. For example, the report may include a graph of the temperature versus the distance run and may identify that the user typically runs the longest distances when the temperature is between 10 C and 15 C. Alternatively, the graph may track the user's average heart rate versus weather type (e.g., sunny, cloudy, rainy, or snowy) and temperature and may note that the user's average heart rate typically enters an optimal "target heart rate" range if the user runs when the weather is cloudy and the temperature is between 7 C and 12 C.

As used herein, the phrase "real-time" may refer to without any intentional delay. However, delay may still occur, for example, due to network-based delay or processor-based delay. One action may occur "in real-time" after another action if it occurs within one second, one minute, one hour, etc., of the other action, as long as the delay is due to processing and network latency, and not due to intentional backlogging.

Figure 4:
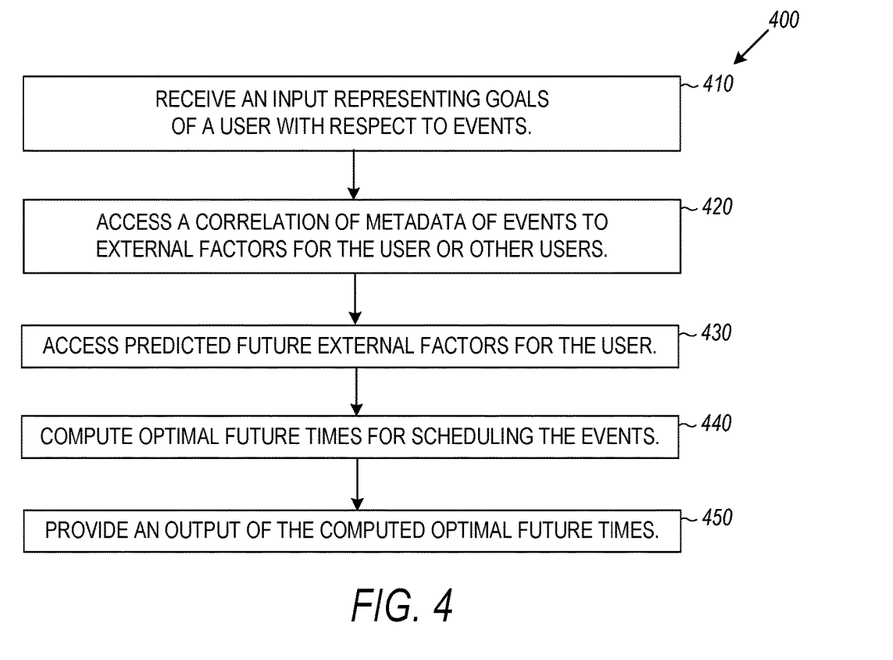
FIG. 4 is a flow chart illustrating an example method for computing optimal times for events, in accordance with some embodiments.

FIG. 4 is a flow chart illustrating an example method 400 for computing optimal times for events, in accordance with some embodiments. The method 400 may be implemented at a machine, such as the client device 110 or the server 120.

At operation 410, the machine receives an input representing goals of a user with respect to events. The events include one or more of a run event, a sleep event, a bike event, and a workout event. In some cases, the goals include a goal related to event metadata (e.g., to run a mile in 10 minutes) or a goal related to a number of events during a future time period (e.g., to work out twice in the next week and run three times in the next week).

At operation 420, the machine accesses a correlation of metadata of events to external factors for the user or other users. The correlation may be determined using all or a portion of the method 300. The external factors include one or more of weather, travel, allergies, diet, and daylight. In some cases, if little information about the user is available to the machine (e.g., if the user has been uploading his/her data to the machine or other machines accessible to the machine for less than one year), the data of other users is accessed. Otherwise, only data about the user is accessed. The other users are identified based on the other users having an age within a threshold number of years (e.g., ten years) of the user, the other users having a same gender as the specified user, or the other users having a common geographic location (e.g., in the state of Connecticut) with the user.

At operation 430, the machine accesses predicted future external factors for the user. For example, the machine may access the user's travel and business plans from the user's calendar. The machine may access a weather and daylight hours forecast for the user's default geographic location or for a geographic location to which the user is travelling. The predicted future external factors may be accessed from a data repository 130. The data repository 130 may include a data storage unit associated with a weather forecaster, a calendar application, or a travel reservation manager.

At operation 440, the machine computes, based on the correlation and the predicted future external factors, optimal future times for scheduling the events. The optimal future times may be computed, using the correlation, to optimize metadata of the events. In one example, the correlation indicates that the user runs the fastest on cloudy days with a temperature between 12 C and 16 C, the user's goals are to run three times in the next week, and there are predicted to be four such days in the next week. The user's runs for the next week may be scheduled for three of the days which are predicted to be cloudy and between 12 C and 16 C.

At operation 450, the machine provides an output of the computed optimal future times. The output may be provided for display via a display unit of a client device 110. Alternatively, the output may be provided as a calendar invite or calendar event in a calendar application accessible via the client device 110.

Figure 5:
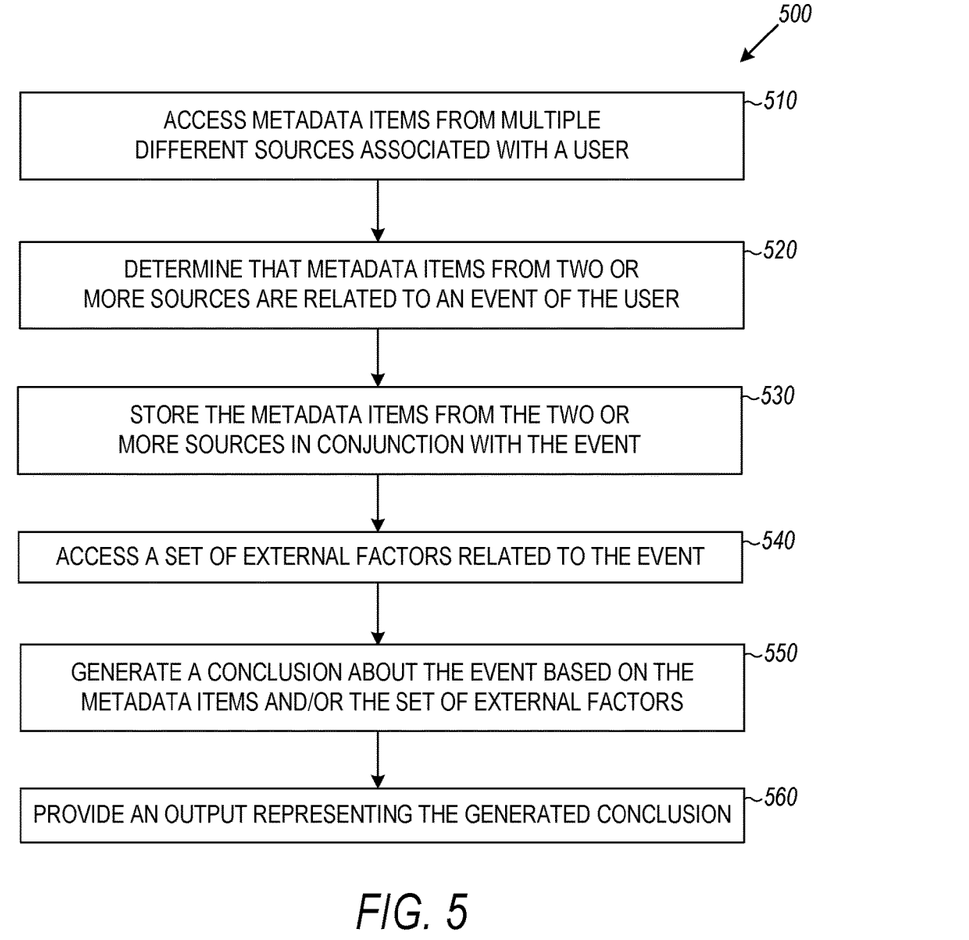
FIG. 5 is a flow chart illustrating an example method for synthesizing data from multiple different sources, in accordance with some embodiments.

FIG. 5 is a flow chart illustrating an example method 500 for synthesizing data from multiple different sources, in accordance with some embodiments. The method 500 is described herein as being implemented at the server 120 within the system 100. However, in alternative embodiments, the method 500 may be implemented at other machine(s) in other system(s).

At operation 510, the server 120 accesses metadata items from multiple different sources associated with a user. The multiple different sources may include client device(s) 110 or wearable device(s) 110 associated with a user. Alternatively, the multiple different sources may include medical data obtained by a medical provider (e.g., a heart rate taken by a nurse during a visit to a physician's office) and stored in a data repository 130.

At operation 520, the server 120 determines that metadata items from two or more sources (from among the multiple different sources) are related to an event (e.g., a physiological activity, such as an exercise performance or performance in a goal-related activity) of the user. The event may be any physiological activity, physiological occasion, or other physiological occurrence, for example, a run event, a sleep event, a bike event, or a workout event. The terms "event" and "occurrence" may be used interchangeably. According to some examples, the server 120 determines that the metadata items are related to the event/occurrence because the metadata items occur contemporaneously with the event/occurrence. For example, if the event/occurrence is a sleep event during the night of Feb. 1-2, 2017, the user may use a mobile phone application to monitor that the user went to bed at 11 PM on February 1 and got up at 7 AM on February 2. The mobile phone application may track how many times the user woke up during the night. During the night, the user may wear a heart rate tracker that tracks his/her heartrate. Based on the time of the heartrate measurements and the time of the sleep event from the mobile phone application, the server 120 may associate the heartrate measurements with the sleep event.

Alternatively, the server 120 determines that the metadata items are related to the event/occurrence because the metadata items are related to a common metric. For example, if the event is a walk event on Feb. 3, 2017, the user's walking may be tracked by a health application on the user's mobile phone (e.g., when the mobile phone is on the user's person) and by a fitness tracker (e.g., when the user is wearing the fitness tracker). According to one example, the day of Feb. 3, 2017 may be divided into five minute increments. For each increment, the server 120 may determine whether the fitness tracker or the mobile phone provided information about walking. If one device provided information about walking but the other did not, then the distance walked is considered as part of the distance walked during the day. This may happen, for example, if the user had one device on him/herself but lacked the other device. Alternatively, if both devices provided data then the data from only one of the devices (e.g., the more accurate device) may be considered or the data from the two devices may be somehow combined (e.g., averaged). That way, a part of the distance walked is not double-counted if it is recorded by both the fitness tracker and the mobile phone.

In some cases, the server 120 gathers, from the multiple different sources, all the metadata that is associated with the event in order to gather as full a picture of the event as possible for making insights and conclusions. The metadata that is associated with the event may be identified based on the common metric or the contemporaneous time.

At operation 530, the server 120 stores the metadata items from the two or more sources in conjunction with the event/occurrence. The storing is in response to determining that the metadata items are associated with the event/occurrence. The server 120 may provide an output representing the event/occurrence and the metadata items. For example, a display of the user's event(s) and metadata items for those events may be provided to one of the user's client devices 110.

At operation 540, the server 120 accesses, from one or more data repositories 130, a set of external factors related to the event/occurrence. The set of external factors may include, for example, weather information, travel information of the user, allergy information about the user and his/her geographic region, diet information, or daylight information. In some cases, the set of external factors occurs contemporaneously and in a common geographic location with the event/occurrence. In some cases, an event/occurrence that has already been processed may be re-processed (according to the method 500) at a later time, for example, when additional metadata or external factors become available. For example, in some cases, metadata from one client device (e.g., a mobile phone) may be provided to the server 120 every minute, while metadata from another client device (e.g., a fitness tracker) may be provided to the server 120 every week or every two weeks. When the metadata from the other client device (e.g., the fitness tracker) is provided, the event(s) may be re-processed to account for the metadata from the other client device.

In one specific example, the event/occurrence is a sleep event on a specified night. The metadata items include a heart rate from a wearable heart rate tracker, a sleep start time from a mobile phone, a sleep end time from the mobile phone, and a number of times woken up during the night from the mobile phone. The set of external factors includes calendar events of the user from a day preceding the specified night (e.g., to indicate how busy and stressed the user was) and weather in a geographic location of the user during the specified night and during the day preceding the specified night.

At operation 550, the server 120 generates a conclusion about the event/occurrence based on the metadata items and/or the set of external factors. The conclusion about the event/occurrence may represent a quality of the event, and the quality of the event may be informed by the metadata items. For example, if the event is a sleep event, and the metadata indicates that the user did not wake up at night and had a heartrate associated with deep sleep, the conclusion may be that the user slept well. If the external factors indicate that the humidity in the user's geographic location was below average, and people typically sleep better in low humidity, the conclusion may be that the user slept well due to the low humidity, and the user may be advised to reduce the humidity of his/her bedroom (e.g., by acquiring a dehumidifier or an air conditioner) in order to improve his/her sleep quality more regularly.

At operation 560, the server 120 provides an output representing the generated conclusion. The output may be provided to a client device 110 of the user (which may correspond to one of the multiple different sources).

In some cases, data from the multiple different sources and/or the data repositories 130 may become available at different times. For instance, in the sleep example, the mobile phone may be uploading metadata (e.g., sleep start time, sleep end time, number of times woken up) to the server 120 once every hour and the wearable heartrate tracker may upload heartrate data to the server 120 once every week. In this case, the sleep event may be reprocessed, and new conclusions may be generated about the sleep event when the heartrate data becomes available.

NUMBERED EXAMPLES

Certain embodiments are described herein as numbered examples 1, 2, 3, etc. These numbered examples are provided as examples only and do not limit the subject technology.

Example 1 is a system comprising: one or more processors; and a memory comprising instructions which, when executed by the one or more processors, cause the one or more processors to perform operations comprising: accessing metadata related to a set of events, the metadata related to the set of events being generated via a client device or a wearable device; accessing, from one or more data repositories distinct from the client device or the wearable device, a set of external factors related to the set of events; correlating, using the one or more processors, the metadata related to the set of events with one or more external factors to generate a correlation; and transmitting an output representing the generated correlation for display.

Example 2 is the system of Example 1, wherein the set of events comprises one or more of: a run event, a sleep event, a bike event, or a workout event, and wherein the set of external factors comprises one or more of: weather, travel, allergies, diet, or daylight.

Example 3 is the system of any of Examples 1-2, wherein the set of external factors occur contemporaneously with the set of events.

Example 4 is the system of any of Examples 1-3, wherein the set of external factors are associated with a same geographic location as the set of events.

Example 5 is the system of any of Examples 1-4, wherein the output representing the generated correlation comprises a graph illustrating metadata of the set of events and the one or more external factors.

Example 6 is the system of any of Examples 1-5, wherein the set of events comprises a run event, wherein the set of external factors comprises an ambient temperature in a geographic region of the client device, and wherein the output comprises a graph of the ambient temperature versus a distance run and a graph of the ambient temperature versus an average running speed.

Example 7 is the system of any of Examples 1-6, wherein the set of events comprises a sleep event, wherein the set of external factors comprises a pollen count in a geographic region of the client device, and wherein the output comprises a graph of the pollen count versus a number of hours of deep sleep.

Example 8 is a non-transitory machine-readable medium comprising instructions which, when executed by one or more processors of a machine, cause the one or more processors to perform operations comprising: accessing metadata related to a set of events, the metadata related to the set of events being generated via a client device or a wearable device; accessing, from one or more data repositories distinct from the client device or the wearable device, a set of external factors related to the set of events; correlating, using the one or more processors, the metadata related to the set of events with one or more external factors to generate a correlation; and transmitting an output representing the generated correlation for display.

Example 9 is the machine-readable medium of Example 8, wherein the set of events comprises one or more of: a run event, a sleep event, a bike event, or a workout event, and wherein the set of external factors comprises one or more of: weather, travel, allergies, diet, or daylight.

Example 10 is the machine-readable medium of any of Example 8-9, wherein the set of external factors occur contemporaneously with the set of events.

Example 11 is the machine-readable medium of any of Example 8-10, wherein the set of external factors are associated with a same geographic location as the set of events.

Example 12 is the machine-readable medium of any of Examples 8-11, wherein the output representing the generated correlation comprises a graph illustrating metadata of the set of events and the one or more external factors.

Example 13 is the machine-readable medium of any of Examples 8-12, wherein the set of events comprises a run event, wherein the set of external factors comprises an ambient temperature in a geographic region of the client device, and wherein the output comprises a graph of the ambient temperature versus a distance run and a graph of the ambient temperature versus an average running speed.

Example 14 is the machine-readable medium of any of Examples 8-13, wherein the set of events comprises a sleep event, wherein the set of external factors comprises a pollen count in a geographic region of the client device, and wherein the output comprises a graph of the pollen count versus a number of hours of deep sleep.

Example 15 is a method implemented at one or more processors of a machine, the method comprising: accessing, at the one or more processors, metadata related to a set of events, the metadata related to the set of events being generated via a client device or a wearable device; accessing, at the one or more processors and from one or more data repositories distinct from the client device or the wearable device, a set of external factors related to the set of events; correlating, using the one or more processors, the metadata related to the set of events with one or more external factors to generate a correlation; and transmitting an output representing the generated correlation for display.

Example 16 is the method of Example 15, wherein the set of events comprises one or more of: a run event, a sleep event, a bike event, or a workout event, and wherein the set of external factors comprises one or more of: weather, travel, allergies, diet, or daylight.

Example 17 is the method of any of Examples 15-16, wherein the set of external factors occur contemporaneously with the set of events.

Example 18 is the method of any of Examples 15-17, wherein the set of external factors are associated with a same geographic location as the set of events.

Example 19 is the method of any of Examples 15-18, wherein the output representing the generated correlation comprises a graph illustrating metadata of the set of events and the one or more external factors.

Example 20 is the method of any of Examples 15-19, wherein the set of events comprises a run event, wherein the set of external factors comprises an ambient temperature in a geographic region of the client device, and wherein the output comprises a graph of the ambient temperature versus a distance run and a graph of the ambient temperature versus an average running speed.

Example 21 is a system comprising: one or more processors; and a memory comprising instructions which, when executed by the one or more processors, cause the one or more processors to perform operations comprising: receiving, at the one or more processors and from a client device or a wearable device of a specified user, metadata about an event of the specified user; accessing, from one or more data repositories distinct from the client device or the wearable device, external factors related to the event of the specified user; accessing metadata about other events and external factors related to the other events of the specified user or of one or more different users; correlating event metadata with the external factors to generate a correlation; determining, based on the generated correlation, how the external factors related to the event of the specified user impacted the metadata about the event of the specified user to generate a report; and providing an output of the generated report, the output being provided in real-time upon receiving the metadata about the event of the specified user.

Example 22 is the system of Example 21, wherein the event comprises one of: a run event, a sleep event, a bike event, or a workout event, and wherein the external factors comprise one or more of: weather, travel, allergies, diet, or daylight.

Example 23 is the system of any of Examples 21-22, wherein the external factors occur contemporaneously with the event.

Example 24 is the system of any of Examples 21-23, wherein the one or more different users are identified based on the one or more different users having an age within a threshold number of years of the specified user, the one or more different users having a same gender as the specified user, or the one or more different users having a common geographic location with the specified user.

Example 25 is the system of any of Examples 21-24, wherein the report comprises a graph of one of the external factors versus the metadata about the event.

Example 26 is the system of any of Examples 21-25, wherein the report identifies optimal conditions, relative to the external factors, for optimizing the metadata of the event.

Example 27 is the system of Example 26, wherein optimizing the metadata of the event comprises minimizing or maximizing the metadata of the event.

Example 28 is a non-transitory machine-readable medium comprising instructions which, when executed by one or more processors of a machine, cause the one or more processors to perform operations comprising: receiving, at the one or more processors and from a client device or a wearable device of a specified user, metadata about an event of the specified user; accessing, from one or more data repositories distinct from the client device or the wearable device, external factors related to the event of the specified user; accessing metadata about other events and external factors related to the other events of the specified user or of one or more different users; correlating event metadata with the external factors to generate a correlation; determining, based on the generated correlation, how the external factors related to the event of the specified user impacted the metadata about the event of the specified user to generate a report; and providing an output of the generated report, the output being provided in real-time upon receiving the metadata about the event of the specified user.

Example 29 is the machine-readable medium of Example 28, wherein the event comprises one of: a run event, a sleep event, a bike event, or a workout event, and wherein the external factors comprise one or more of: weather, travel, allergies, diet, or daylight.

Example 30 is the machine-readable medium of any of Examples 28-29, wherein the external factors occur contemporaneously with the event.

Example 31 is the machine-readable medium of any of Examples 28-30, wherein the one or more different users are identified based on the one or more different users having an age within a threshold number of years of the specified user, the one or more different users having a same gender as the specified user, or the one or more different users having a common geographic location with the specified user.

Example 32 is the machine-readable medium of any of Examples 28-31, wherein the report comprises a graph of one of the external factors versus the metadata about the event.

Example 33 is the machine-readable medium of any of Example 28-32, wherein the report identifies optimal conditions, relative to the external factors, for optimizing the metadata of the event.

Example 34 is the machine-readable medium of Example 33, wherein optimizing the metadata of the event comprises minimizing or maximizing the metadata of the event.

Example 35 is a method implemented at one or more processors of a machine, the method comprising: receiving, at the one or more processors and from a client device or a wearable device of a specified user, metadata about an event of the specified user; accessing, from one or more data repositories distinct from the client device or the wearable device, external factors related to the event of the specified user; accessing metadata about other events and external factors related to the other events of the specified user or of one or more different users; correlating event metadata with the external factors to generate a correlation; determining, based on the generated correlation, how the external factors related to the event of the specified user impacted the metadata about the event of the specified user to generate a report; and providing an output of the generated report, the output being provided in real-time upon receiving the metadata about the event of the specified user.

Example 36 is the method of Example 35, wherein the event comprises one of: a run event, a sleep event, a bike event, or a workout event, and wherein the external factors comprise one or more of: weather, travel, allergies, diet, or daylight.

Example 37 is the method of any of Examples 35-36, wherein the external factors occur contemporaneously with the event.

Example 38 is the method of any of Examples 35-37, wherein the one or more different users are identified based on the one or more different users having an age within a threshold number of years of the specified user, the one or more different users having a same gender as the specified user, or the one or more different users having a common geographic location with the specified user.

Example 39 is the method of any of Examples 35-38, wherein the report comprises a graph of one of the external factors versus the metadata about the event.

Example 40 is the method of any of Examples 35-39, wherein the report identifies optimal conditions, relative to the external factors, for optimizing the metadata of the event.

Example 41 is a system comprising: one or more processors; and a memory comprising instructions which, when executed by the one or more processors, cause the one or more processors to perform operations comprising: receiving, at the one or more processors, an input representing goals of a user with respect to events; accessing, at the one or more processors, a correlation of metadata of events to external factors for the user or other users; accessing, at the one or more processors, predicted future external factors for the user; computing, based on the correlation and the predicted future external factors, optimal future times for scheduling the events; and providing an output of the computed optimal future times.

Example 42 is the system of Example 41, wherein the events comprises one or more of: a run event, a sleep event, a bike event, or a workout event, and wherein the external factors comprises one or more of: weather, travel, allergies, diet, or daylight.

Example 43 is the system of any of Examples 41-42, wherein the goals of the user with respect to the events comprise a goal related to event metadata or a goal related to a number of events during a future time period.

Example 44 is the system of any of Examples 41-43, the operations further comprising: receiving, at the one or more processors and from a client device or a wearable device of the user, metadata about events of the user; accessing, from one or more data repositories distinct from the client device or the wearable device, past external factors related to the events of the user; accessing metadata about other events and external factors related to the other events of the user or the other users; and correlating event metadata with the external factors to generate the accessed correlation.

Example 45 is the system of any of Examples 41-44, wherein the other users are identified based on the one other users having an age within a threshold number of years of the user, the other users having a same gender as the user, or the other users having a common geographic location with the user.

Example 46 is the system of any of Examples 41-45, wherein the predicted future external factors are accessed via a weather forecast, a calendar application, or a travel reservation manager.

Example 47 is the system of Example 41-46, wherein the optimal future times for scheduling the events are computed, using the correlation, to optimize metadata of the events.

Example 48 is a non-transitory machine-readable medium comprising instructions which, when executed by one or more processors of a machine, cause the one or more processors to perform operations comprising: receiving, at the one or more processors, an input representing goals of a user with respect to events; accessing, at the one or more processors, a correlation of metadata of events to external factors for the user or other users; accessing, at the one or more processors, predicted future external factors for the user; computing, based on the correlation and the predicted future external factors, optimal future times for scheduling the events; and providing an output of the computed optimal future times.

Example 49 is the machine-readable medium of Example 48, wherein the events comprises one or more of: a run event, a sleep event, a bike event, or a workout event, and wherein the external factors comprises one or more of: weather, travel, allergies, diet, or daylight.

Example 50 is the machine-readable medium of any of Examples 48-49, wherein the goals of the user with respect to the events comprise a goal related to event metadata or a goal related to a number of events during a future time period.

Example 51 is the machine-readable medium of any of Examples 48-50, the operations further comprising: receiving, at the one or more processors and from a client device or a wearable device of the user, metadata about events of the user; accessing, from one or more data repositories distinct from the client device or the wearable device, past external factors related to the events of the user; accessing metadata about other events and external factors related to the other events of the user or the other users; and correlating event metadata with the external factors to generate the accessed correlation.

Example 52 is the machine-readable medium of any of Examples 48-51, wherein the other users are identified based on the one other users having an age within a threshold number of years of the user, the other users having a same gender as the user, or the other users having a common geographic location with the user.

Example 53 is the machine-readable medium of any of Examples 48-52, wherein the predicted future external factors are accessed via a weather forecast, a calendar application, or a travel reservation manager.

Example 54 is the machine-readable medium of any of Examples 48-53, wherein the optimal future times for scheduling the events are computed, using the correlation, to optimize metadata of the events.

Example 55 is a method implemented at one or more processors of a machine, the method comprising: receiving, at the one or more processors, an input representing goals of a user with respect to events; accessing, at the one or more processors, a correlation of metadata of events to external factors for the user or other users; accessing, at the one or more processors, predicted future external factors for the user; computing, based on the correlation and the predicted future external factors, optimal future times for scheduling the events; and providing an output of the computed optimal future times.

Example 56 is the method of Example 55, wherein the events comprises one or more of: a run event, a sleep event, a bike event, or a workout event, and wherein the external factors comprises one or more of: weather, travel, allergies, diet, or daylight.

Example 57 is the method of any of Examples 55-56, wherein the goals of the user with respect to the events comprise a goal related to event metadata or a goal related to a number of events during a future time period.

Example 58 is the method of any of Examples 55-57, further comprising: receiving, at the one or more processors and from a client device or a wearable device of the user, metadata about events of the user; accessing, from one or more data repositories distinct from the client device or the wearable device, past external factors related to the events of the user; accessing metadata about other events and external factors related to the other events of the user or the other users; and correlating event metadata with the external factors to generate the accessed correlation.

Example 59 is the method of any of Examples 55-58, wherein the other users are identified based on the one other users having an age within a threshold number of years of the user, the other users having a same gender as the user, or the other users having a common geographic location with the user.

Example 60 is the method of any of Examples 55-59, wherein the predicted future external factors are accessed via a weather forecast, a calendar application, or a travel reservation manager.

Example 61 is a system comprising: one or more processors; and a memory comprising instructions which, when executed by the one or more processors, cause the one or more processors to perform operations comprising: accessing metadata items from multiple different sources associated with a user; determining that metadata items from two or more sources are related to an event of the user, the two or more sources being from among the multiple different sources; storing the metadata items from the two or more of the sources in conjunction with the event; generating a conclusion about the event based on the metadata items stored in conjunction with the event; and providing, to a computing device, an output representing the generated conclusion.

Example 62 is the system of Example 61, the operations further comprising: accessing, from one or more data repositories, a set of external factors related to the event, wherein the conclusion about the event is generate based on the set of external factors.

Example 63 is the system of Example 62, wherein: the set of external factors comprises one or more of: weather, travel, allergies, diet, or daylight; the set of external factors occur contemporaneously and in a common geographic location with the event; and the one or more data repositories are distinct from the multiple different sources.

Example 64 is the system of any of Examples 62-63, wherein: the event comprises a sleep event on a specified night; the metadata items comprise a heart rate from a wearable heart rate tracker, a sleep start time from a mobile phone, a sleep end time from the mobile phone, and a number of times woken up during the night from the mobile phone; and the set of external factors comprises calendar events of the user from a day preceding the specified night and weather in a geographic location of the user during the specified night and during the day preceding the specified night.

Example 65 is the system of any of Examples 61-64, wherein the multiple different sources comprise one or more client devices or one or more wearable devices associated with the user.

Example 66 is the system of Example 65, wherein the one or more client devices comprise the computing device.

Example 67 is the system of any of Examples 61-66, wherein the event comprises one or more of: a run event, a sleep event, a bike event, or a workout event.

Example 68 is the system of any of Examples 61-67, wherein the conclusion about the event represents a quality of the event, the quality of the event being informed by the metadata items.

Example 69 is the system of any of Examples 61-68, wherein determining that the metadata items from the two or more sources are related to the event of the user comprises: determining that the two or more metadata items occur contemporaneously or determining that the two or more metadata items are associated with a common metric.

Example 70 is the system of Example 69, wherein the common metric comprises a number of steps taken during a predefined time period or a distance walked during the predefined time period.

Example 71 is a non-transitory machine-readable medium comprising instructions which, when executed by one or more processors of a machine, cause the one or more processors to perform operations comprising: accessing metadata items from multiple different sources associated with a user; determining that metadata items from two or more sources are related to an event of the user, the two or more sources being from among the multiple different sources; storing the metadata items from the two or more of the sources in conjunction with the event; generating a conclusion about the event based on the metadata items stored in conjunction with the event; and providing, to a computing device, an output representing the generated conclusion.

Example 72 is the machine-readable medium of Example 71, the operations further comprising: accessing, from one or more data repositories, a set of external factors related to the event, wherein the conclusion about the event is generate based on the set of external factors.

Example 73 is the machine-readable medium of Example 72, wherein: the set of external factors comprises one or more of: weather, travel, allergies, diet, or daylight; the set of external factors occur contemporaneously and in a common geographic location with the event; and the one or more data repositories are distinct from the multiple different sources.

Example 74 is the machine-readable medium of any of Examples 72-73, wherein: the event comprises a sleep event on a specified night; the metadata items comprise a heart rate from a wearable heart rate tracker, a sleep start time from a mobile phone, a sleep end time from the mobile phone, and a number of times woken up during the night from the mobile phone; and the set of external factors comprises calendar events of the user from a day preceding the specified night and weather in a geographic location of the user during the specified night and during the day preceding the specified night.

Example 75 is the machine-readable medium of any of Examples 71-74, wherein the multiple different sources comprise one or more client devices or one or more wearable devices associated with the user.

Example 76 is the machine-readable medium of any of Examples 71-75, wherein the event comprises one or more of: a run event, a sleep event, a bike event, or a workout event.

Example 77 is the machine-readable medium of any of Examples 71-76, wherein the conclusion about the event represents a quality of the event, the quality of the event being informed by the metadata items.

Example 78 is a method comprising: accessing metadata items from multiple different sources associated with a user; determining that metadata items from two or more sources are related to an event of the user, the two or more sources being from among the multiple different sources; storing the metadata items from the two or more of the sources in conjunction with the event; generating a conclusion about the event based on the metadata items stored in conjunction with the event; and providing, to a computing device, an output representing the generated conclusion.

Example 79 is the method of Example 78, the operations further comprising: accessing, from one or more data repositories, a set of external factors related to the event, wherein the conclusion about the event is generate based on the set of external factors.

Example 80 is the method of Example 79, wherein: the set of external factors comprises one or more of: weather, travel, allergies, diet, or daylight; the set of external factors occur contemporaneously and in a common geographic location with the event; and the one or more data repositories are distinct from the multiple different sources.

Components and Logic

Certain embodiments are described herein as including logic or a number of components or mechanisms. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

In some embodiments, a hardware component may be implemented mechanically, electronically, or any suitable combination thereof. For example, a hardware component may include dedicated circuitry or logic that is permanently configured to perform certain operations. For example, a hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations.

Accordingly, the phrase "hardware component" should be understood to encompass a tangible record, be that an record that is physically constructed, permanently configured (e.g., hardwired), or temporarily configured (e.g., programmed) to operate in a certain manner or to perform certain operations described herein. As used herein, "hardware-implemented component" refers to a hardware component. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors.

Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API).

The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

Some aspects of the subject technology involve collecting personal information about users. It should be noted that the personal information about a user is collected after receiving affirmative consent from the users for the collection and storage of such information. Persistent reminders (e.g., email messages or information displays within an application) are provided to the user to notify the user that his/her information is being collected and stored. The persistent reminders may be provided whenever the user accesses an application or once every threshold time period (e.g., an email message every week). For instance, an arrow symbol may be displayed to the user on his/her mobile device to notify the user that his/her global positioning system (GPS) location is being tracked. Personal information is stored in a secure manner to ensure that no unauthorized access to the information takes place. For example, medical and health related information may be stored in a Health Insurance Portability and Accountability Act (HIPAA) compliant manner.

Example Machine and Software Architecture

The components, methods, applications, and so forth described in conjunction with FIGS. 1-4 are implemented in some embodiments in the context of a machine and an associated software architecture. The sections below describe representative software architecture(s) and machine (e.g., hardware) architecture(s) that are suitable for use with the disclosed embodiments.

Software architectures are used in conjunction with hardware architectures to create devices and machines tailored to particular purposes. For example, a particular hardware architecture coupled with a particular software architecture will create a mobile device, such as a mobile phone, tablet device, or so forth. A slightly different hardware and software architecture may yield a smart device for use in the "internet of things," while yet another combination produces a server computer for use within a cloud computing architecture. Not all combinations of such software and hardware architectures are presented here, as those of skill in the art can readily understand how to implement the inventive subject matter in different contexts from the disclosure contained herein.

Figure 6:
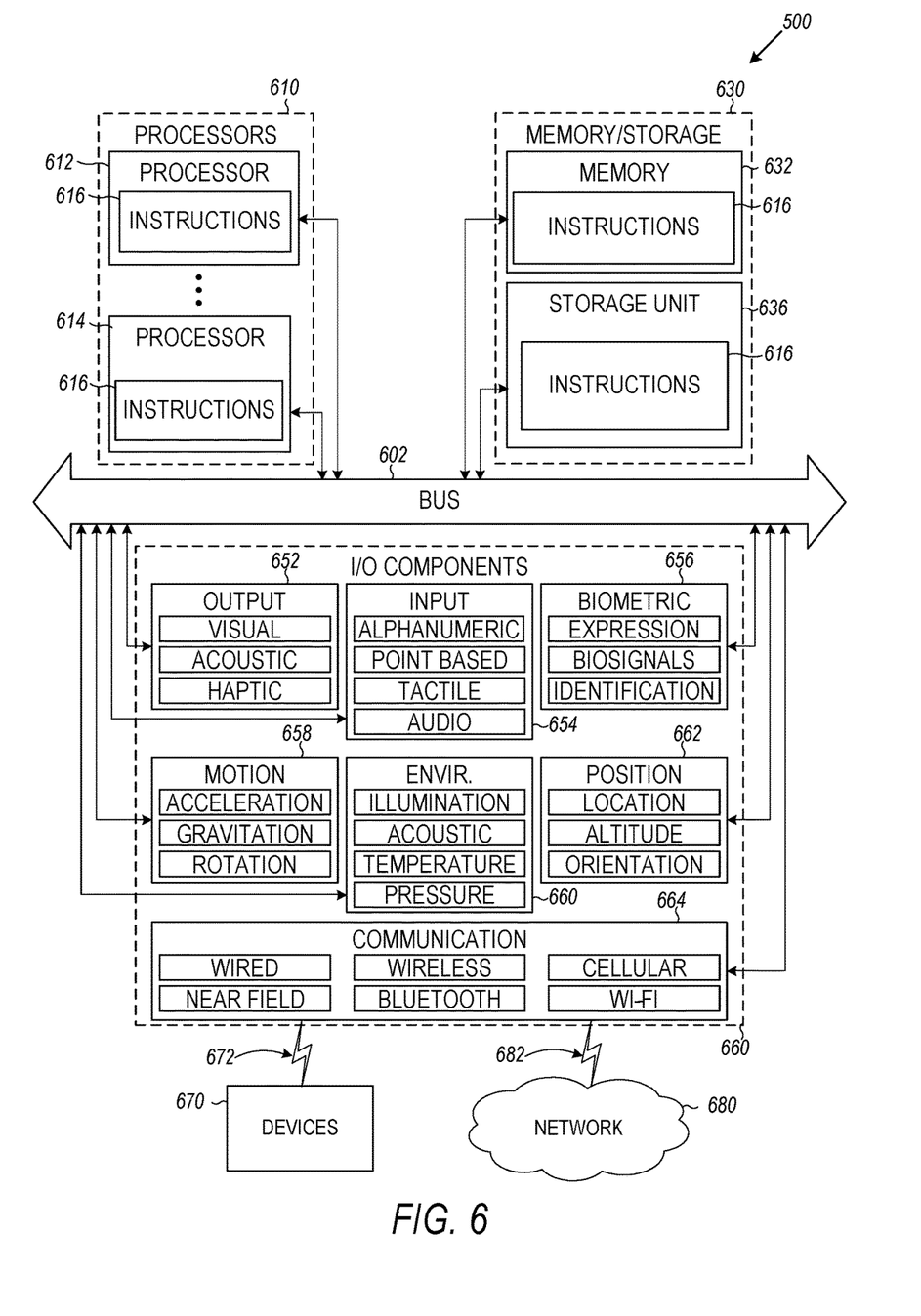
FIG. 6 is a block diagram illustrating components of a machine able to read instructions from a machine-readable medium and perform any of the methodologies discussed herein, in accordance with some embodiments.

FIG. 6 is a block diagram illustrating components of a machine 600, according to some example embodiments, able to read instructions from a machine-readable medium (e.g., a machine-readable storage medium) and perform any one or more of the methodologies discussed herein. Specifically, FIG. 6 shows a diagrammatic representation of the machine 600 in the example form of a computer system, within which instructions 616 (e.g., software, a program, an application, an applet, an app, or other executable code) for causing the machine 600 to perform any one or more of the methodologies discussed herein may be executed. The instructions 616 transform the general, non-programmed machine into a particular machine programmed to carry out the described and illustrated functions in the manner described. In alternative embodiments, the machine 600 operates as a standalone device or may be coupled (e.g., networked) to other machines. In a networked deployment, the machine 600 may operate in the capacity of a server machine or a client machine in a server-client network environment, or as a peer machine in a peer-to-peer (or distributed) network environment. The machine 600 may comprise, but not be limited to, a server computer, a client computer, PC, a tablet computer, a laptop computer, a netbook, a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 616, sequentially or otherwise, that specify actions to be taken by the machine 600. Further, while only a single machine 600 is illustrated, the term "machine" shall also be taken to include a collection of machines 600 that individually or jointly execute the instructions 616 to perform any one or more of the methodologies discussed herein.

The machine 600 may include processors 610, memory/storage 630, and I/O components 650, which may be configured to communicate with each other such as via a bus 602. In an example embodiment, the processors 610 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 612 and a processor 614 that may execute the instructions 616. The term "processor" is intended to include multi-core processors that may comprise two or more independent processors (sometimes referred to as "cores") that may execute instructions contemporaneously. Although FIG. 6 shows multiple processors 610, the machine 600 may include a single processor with a single core, a single processor with multiple cores (e.g., a multi-core processor), multiple processors with a single core, multiple processors with multiples cores, or any combination thereof.

The memory/storage 630 may include a memory 632, such as a main memory, or other memory storage, and a storage unit 636, both accessible to the processors 610 such as via the bus 602. The storage unit 636 and memory 632 store the instructions 616 embodying any one or more of the methodologies or functions described herein. The instructions 616 may also reside, completely or partially, within the memory 632, within the storage unit 636, within at least one of the processors 610 (e.g., within the processor's cache memory), or any suitable combination thereof, during execution thereof by the machine 600. Accordingly, the memory 632, the storage unit 636, and the memory of the processors 610 are examples of machine-readable media.

As used herein, "machine-readable medium" means a device able to store instructions (e.g., instructions 616) and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)), and/or any suitable combination thereof. The term "machine-readable medium" should be taken to include a single medium or multiple media (e.g., a centralized or distributed database, or associated caches and servers) able to store the instructions 616. The term "machine-readable medium" shall also be taken to include any medium, or combination of multiple media, that is capable of storing instructions (e.g., instructions 616) for execution by a machine (e.g., machine 600), such that the instructions, when executed by one or more processors of the machine (e.g., processors 610), cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 650 may include a wide variety of components to receive input, provide output, produce output, transmit information, exchange information, capture measurements, and so on. The specific I/O components 650 that are included in a particular machine will depend on the type of machine. For example, portable machines such as mobile phones will likely include a touch input device or other such input mechanisms, while a headless server machine will likely not include such a touch input device. It will be appreciated that the I/O components 650 may include many other components that are not shown in FIG. 6. The I/O components 650 are grouped according to functionality merely for simplifying the following discussion and the grouping is in no way limiting. In various example embodiments, the I/O components 650 may include output components 652 and input components 654. The output components 652 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 654 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 650 may include biometric components 656, motion components 658, environmental components 660, or position components 662, among a wide array of other components. For example, the biometric components 656 may include components to detect expressions (e.g., hand expressions, facial expressions, vocal expressions, body gestures, or eye tracking), measure biosignals (e.g., blood pressure, heart rate, body temperature, perspiration, or brain waves), measure exercise-related metrics (e.g., distance moved, speed of movement, or time spent exercising) identify a person (e.g., voice identification, retinal identification, facial identification, fingerprint identification, or electroencephalogram based identification), and the like. The motion components 658 may include acceleration sensor components (e.g., accelerometer), gravitation sensor components, rotation sensor components (e.g., gyroscope), and so forth. The environmental components 660 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment. The position components 662 may include location sensor components (e.g., a Global Position System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 650 may include communication components 664 operable to couple the machine 600 to a network 680 or devices 670 via a coupling 682 and a coupling 672, respectively. For example, the communication components 664 may include a network interface component or other suitable device to interface with the network 680. In further examples, the communication components 664 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 670 may be another machine or any of a wide variety of peripheral devices (e.g., a peripheral device coupled via a USB).

Moreover, the communication components 664 may detect identifiers or include components operable to detect identifiers. For example, the communication components 664 may include Radio Frequency Identification (RFID) tag reader components, NFC smart tag detection components, optical reader components, or acoustic detection components (e.g., microphones to identify tagged audio signals). In addition, a variety of information may be derived via the communication components 664, such as location via Internet Protocol (IP) geolocation, location via Wi-Fi® signal triangulation, location via detecting an NFC beacon signal that may indicate a particular location, and so forth.

In various example embodiments, one or more portions of the network 680 may be an ad hoc network, an intranet, an extranet, a virtual private network (VPN), a local area network (LAN), a wireless LAN (WLAN), a WAN, a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, the network 680 or a portion of the network 680 may include a wireless or cellular network and the coupling 682 may be a Code Division Multiple Access (CDMA) connection, a Global System for Mobile communications (GSM) connection, or another type of cellular or wireless coupling. In this example, the coupling 682 may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 616 may be transmitted or received over the network 680 using a transmission medium via a network interface device (e.g., a network interface component included in the communication components 664) and utilizing any one of a number of well-known transfer protocols (e.g., HTTP). Similarly, the instructions 616 may be transmitted or received using a transmission medium via the coupling 672 (e.g., a peer-to-peer coupling) to the devices 670. The term "transmission medium" shall be taken to include any intangible medium that is capable of storing, encoding, or carrying the instructions 616 for execution by the machine 600, and includes digital or analog communications signals or other intangible media to facilitate communication of such software.

What is claimed is:

1. A system comprising:
   one or more processors; and
   a memory comprising instructions which, when executed by the one or more processors, cause the one or more processors to perform operations comprising:
   accessing user metadata from multiple different sources associated with a user;
   determining that metadata items from two or more sources are related to an event of the user, the two or more sources being from among the multiple different sources;
   storing the metadata items from the two or more sources in conjunction with the event;
   accessing, from one or more data repositories, a set of external factors related to the event;
   storing the set of external factors in conjunction with the event, wherein:
   the event comprises a sleep event on a specified night;
   the metadata items comprise a heart rate from a wearable heart rate tracker, a sleep start time from a mobile phone, a sleep end time from the mobile phone, and a number of times woken up during the specified night from the mobile phone; and
   the set of external factors comprises calendar events of the user from a day preceding the specified night, and weather in a geographic location of the user during the specified night and during the day preceding the specified night; and providing, to the user, an output representing the event, the metadata items, and the set of external factors.

2. The system of claim 1, wherein:
the set of external factors comprises one or more of: weather, travel, allergies, diet, or daylight;
the set of external factors occur contemporaneously and in a common geographic location with the event; and
the one or more data repositories are distinct from the multiple different sources.

3. The system of claim 1, wherein the multiple different sources comprise one or more client devices or one or more wearable devices associated with the user.

4. The system of claim 1, wherein the event further comprises one or more of: a run event, a bike event, or a workout event.

5. The system of claim 1, wherein the determining that the metadata items from the two or more sources are related to the event of the user comprises:
determining that the two or more metadata items occur contemporaneously or determining that the two or more metadata items are associated with a common metric.

6. The system of claim 5, wherein the common metric comprises a number of steps taken during a predefined time period or a distance walked during the predefined time period.

7. The system of claim 1, wherein the user metadata comprise two or more metadata items.

8. The system of claim 1, wherein the set of external factors comprises one or more external factors.

9. A non-transitory machine-readable medium comprising instructions which, when executed by one or more processors of a machine, cause the one or more processors to perform operations comprising:
accessing user metadata from multiple different sources associated with a user;
determining that metadata items from two or more sources are related to an event of the user, the two or more sources being from among the multiple different sources;
storing the metadata items from the two or more sources in conjunction with the event;
accessing, from one or more data repositories, a set of external factors related to the event;
storing the set of external factors in conjunction with the event, wherein:
the event comprises a sleep event on a specified night;
the metadata items comprise a heart rate from a wearable heart rate tracker, a sleep start time from a mobile phone, a sleep end time from the mobile phone, and a number of times woken up during the specified night from the mobile phone; and
the set of external factors comprises calendar events of the user from a day preceding the specified night, and weather in a geographic location of the user during the specified night and during the day preceding the specified night; and
providing, to the user, an output representing the event, the metadata items, and the set of external factors.

10. The machine-readable medium of claim 9, wherein:
the set of external factors comprises one or more of: weather, travel, allergies, diet, or daylight;
the set of external factors occur contemporaneously and in a common geographic location with the event; and
the one or more data repositories are distinct from the multiple different sources.

11. The machine-readable medium of claim 9, wherein the multiple different sources comprise one or more client devices or one or more wearable devices associated with the user.

12. The machine-readable medium of claim 9, wherein the event further comprises one or more of: a run event, a bike event, or a workout event.

13. The machine-readable medium of claim 9, wherein the determining that the metadata items from the two or more sources are related to the event of the user comprises:
determining that the two or more metadata items occur contemporaneously or determining that the two or more metadata items are associated with a common metric.

14. The machine-readable medium of claim 13, wherein the common metric comprises a number of steps taken during a predefined time period or a distance walked during the predefined time period.

15. A method implemented by at least one computing device, comprising:
accessing user metadata from multiple different sources associated with a user;
determining that metadata items from two or more sources are related to an event of the user, the two or more sources being from among the multiple different sources;
storing the metadata items from the two or more sources in conjunction with the event;
accessing, from one or more data repositories, a set of external factors related to the event;
storing the set of external factors in conjunction with the event, wherein:
the event comprises a sleep event on a specified night;
the metadata items comprise a heart rate from a wearable heart rate tracker, a sleep start time from a mobile phone, a sleep end time from the mobile phone, and a number of times woken up during the specified night from the mobile phone; and
the set of external factors comprises calendar events of the user from a day preceding the specified night, and weather in a geographic location of the user during the specified night and during the day preceding the specified night; and
providing, to the user, an output representing the event, the metadata items, and the set of external factors.

16. The method of claim 15, wherein:
the set of external factors comprises one or more of: weather, travel, allergies, diet, or daylight;
the set of external factors occur contemporaneously and in a common geographic location with the event; and
the one or more data repositories are distinct from the multiple different sources.

* * * * *